(12) United States Patent
Koyano et al.

(10) Patent No.: US 6,606,897 B1
(45) Date of Patent: Aug. 19, 2003

(54) PORTABLE GAS DETECTOR AND ITS CRADLE

(75) Inventors: Juniti Koyano, Tokyo (JP); Shuji Tajima, Tokyo (JP); Masahide Kitamura, Tokyo (JP)

(73) Assignee: Riken Keiki Co., Ltd., Tokyo (JP)

( * ) Notice: Subject to any disclaimer, the term of this patent is extended or adjusted under 35 U.S.C. 154(b) by 0 days.

(21) Appl. No.: 09/684,320

(22) Filed: Oct. 10, 2000

(51) Int. Cl.[7] .......................... G01N 9/00; G01L 19/14; G01D 11/24; G01D 21/00; G01P 19/14
(52) U.S. Cl. .......................... 73/23.2; 73/31.05; 73/431; 73/866.5
(58) Field of Search .............................. 73/23.2, 23.3, 73/31.05, 31.06, 431, 866.5

(56) References Cited

U.S. PATENT DOCUMENTS

| | | | | |
|---|---|---|---|---|
| 3,877,291 A | * | 4/1975 | Hoppesch et al. | 340/634 |
| 4,578,586 A | * | 3/1986 | Preston | 250/336.1 |
| 4,705,617 A | * | 11/1987 | Beebe et al. | 204/402 |
| 5,501,231 A | * | 3/1996 | Kaish | 600/484 |
| 5,957,854 A | * | 9/1999 | Besson et al. | 128/903 |
| 6,085,576 A | * | 7/2000 | Sunshine et al. | 340/634 |
| 6,198,400 B1 | * | 3/2001 | Church et al. | 340/632 |
| 6,205,840 B1 | * | 3/2001 | Thompson | 422/84 |

FOREIGN PATENT DOCUMENTS

JP             098337     *  4/1990

OTHER PUBLICATIONS

Description from GB 1,573,678 (Aug. 1980), no drawings, from ep.espace.com.*
U.S. patent application Ser. No. 10,201,068, filed Jul. 22, 2002, Junichi Koyano et al., "Gas Suction Pump Device, Gas Feed Adapter and Gas Alarm Unit", Formal Drawings 9–sheets of FIGS. 1–13, Specification 56–pages.

* cited by examiner

*Primary Examiner*—Hezron Williams
*Assistant Examiner*—Michael Cygan
(74) *Attorney, Agent, or Firm*—Connolly Bove Lodge & Hutz LLP (57) ABSTRACT

A portable gas detector comprises a casing proper 1 adapted to be attached to the human body. The casing proper 1 has multiple openings to accommodate gas sensors 5 on one side and charging terminals 38 and a communication window 14 on the other. Calibration of the gas sensors and securing of power supply are easy to achieve.

5 Claims, 11 Drawing Sheets

PORTABLE GAS DETECTOR AND ITS CRADLE

FIELD OF THE INVENTION

This invention relates to a small portable gas detector and a cradle suited for use therewith.

DESCRIPTION OF THE PRIOR ART

A gas detector adapted to be attached to clothing or the body for continuous monitoring of the existence of gases in the work environment comprises gas sensors for different kinds of gases, a power supply and an indicator contained in a small casing.

Used to prevent accidents by detecting the existence of toxic gases in the work environment as early as possible, this type of device is required to have a high degree of reliability.

To insure the desired reliability, each sensor must be capable of sensing the target gas with certainty and adequate supply of electricity is maintained.

SUMMARY OF THE INVENTION

A portable gas detector according to this invention comprises a casing that can be attached to the body, the casing having multiple openings to accommodate said gas sensors on one side thereof and power supply and communication terminals on the other. While calibration of the gas sensors can be accomplished by supplying a reference gas from one side, electrical charging can be made from the other side without interfering with the supply of the reference gas.

An object of this invention, as such, is to provide a portable gas detector that facilitates the calibration of the sensors and the supply of electricity.

Another object of this invention is to provide a cradle suited for use with the portable gas detector of the type described above.

DESCRIPTION OF THE PREFERRED EMBODIMENTS

Figure 1A:
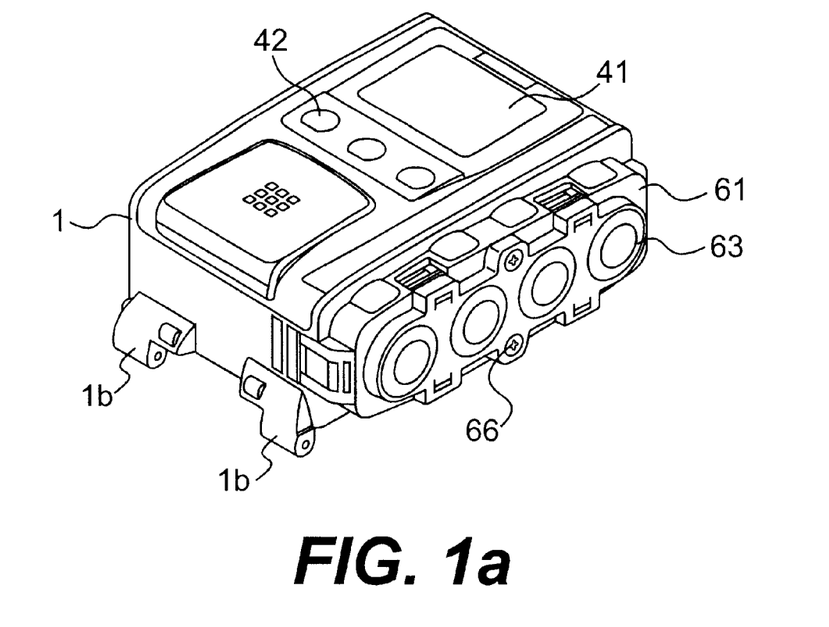
FIGS. 1a and 1b are perspective views of a small gas detector embodying the concept of this invention.
Figure 1B:
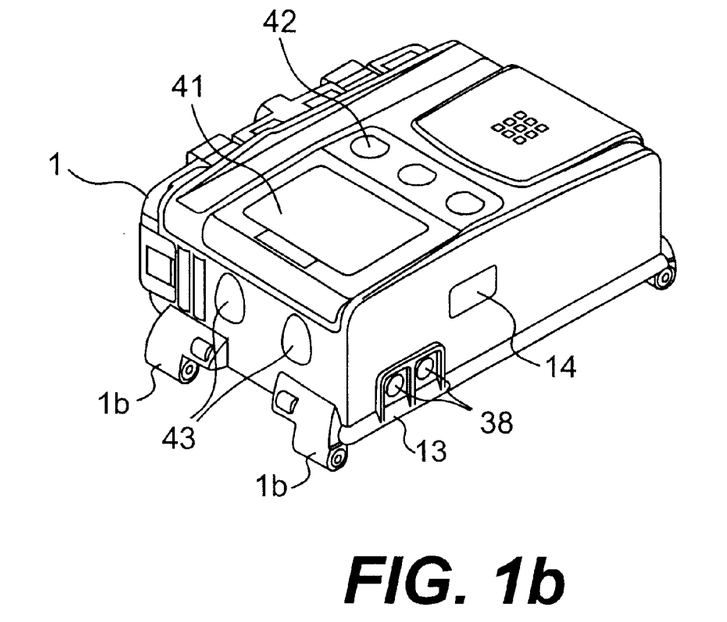
Figure 2A:
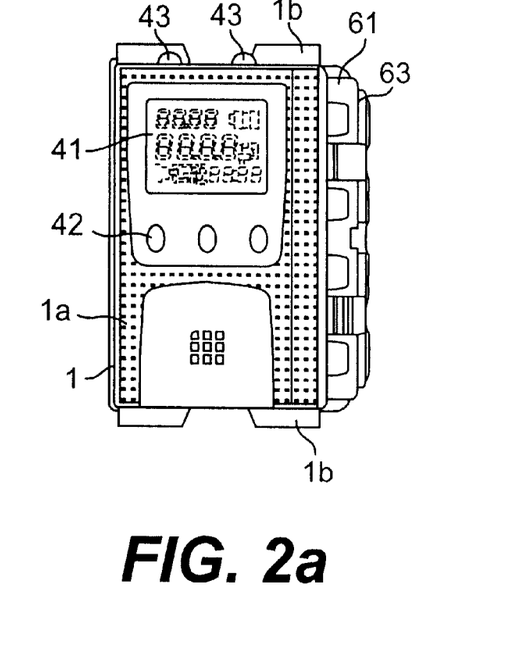
FIGS. 2a to 2c are a front view, a left side elevation and a right side elevation of the same gas detector.
Figure 2B:
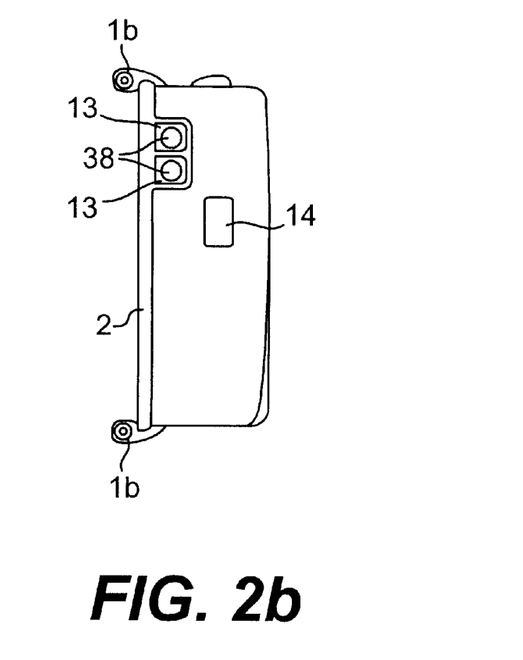
Figure 2C:
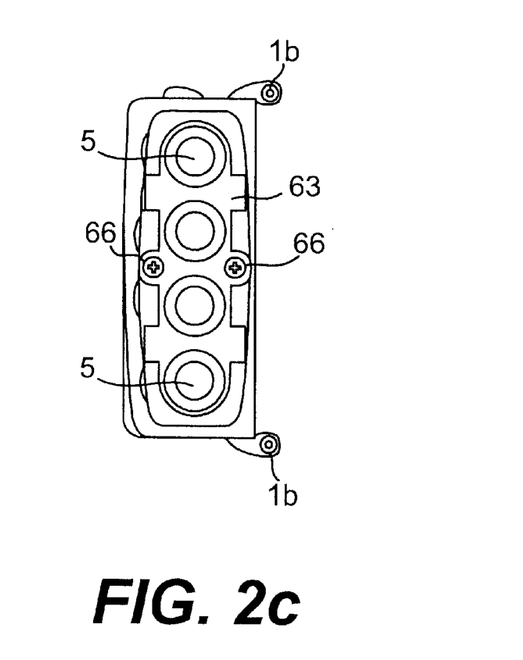
Figure 3:
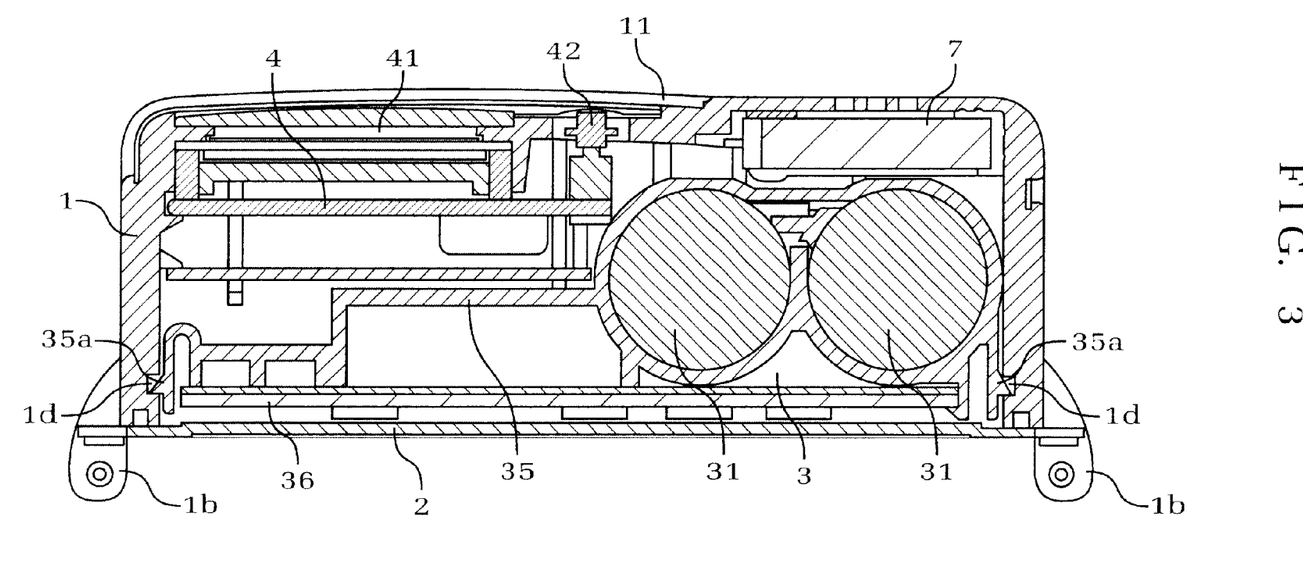
FIG. 3 is a cross-sectional view of the same gas detector.

FIGS. 1 to 3 show an embodiment of the small gas detector according to this invention comprising a casing proper 1 made of injection-molded high polymer and an electrically conductive cover 2. A power supply unit 3, a signal-processing unit 4 and a sound generating element 7 are accommodated. A metal sheet 1a (an area indicated by dots in FIG. 2), which also serves as an ornament, is integrally buried in the surface of the casing proper 1 by insert molding. Placing the metal sheet 1a over the surface of the static-prone casing proper 1 made of high polymer curbs the production of static electricity as much as possible and, thereby, provides assurance of the safe use of the gas detector even in the presence of combustible gases.

Band receptacles 1b formed at both ends of the casing proper 1 receives a band fastened thereto whereby the gas detector is worn on the wrist.

The signal-processing unit 4 comprises a memory element storing log data, a liquid-crystal display panel 41, external control switches 42 and light-emitting elements 43. The liquid-crystal display panel 41 is fastened in the casing proper 1 so as to be exposed to the outside through a window 11 in the casing proper 1.

Figure 4:
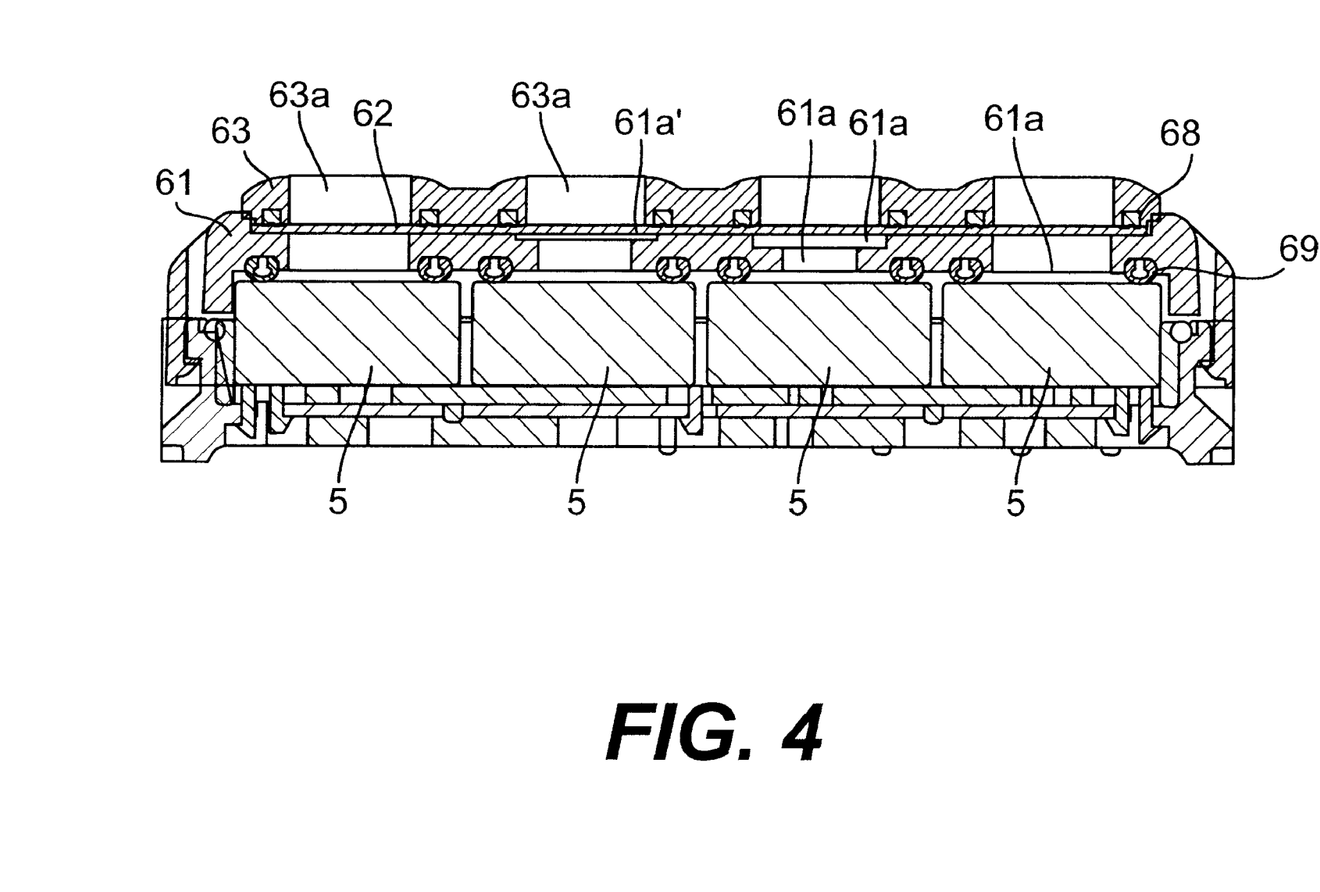
FIG. 4 is a cross-sectional view showing an embodiment of a gas-sensor holder in the same gas detector.
Figure 5:
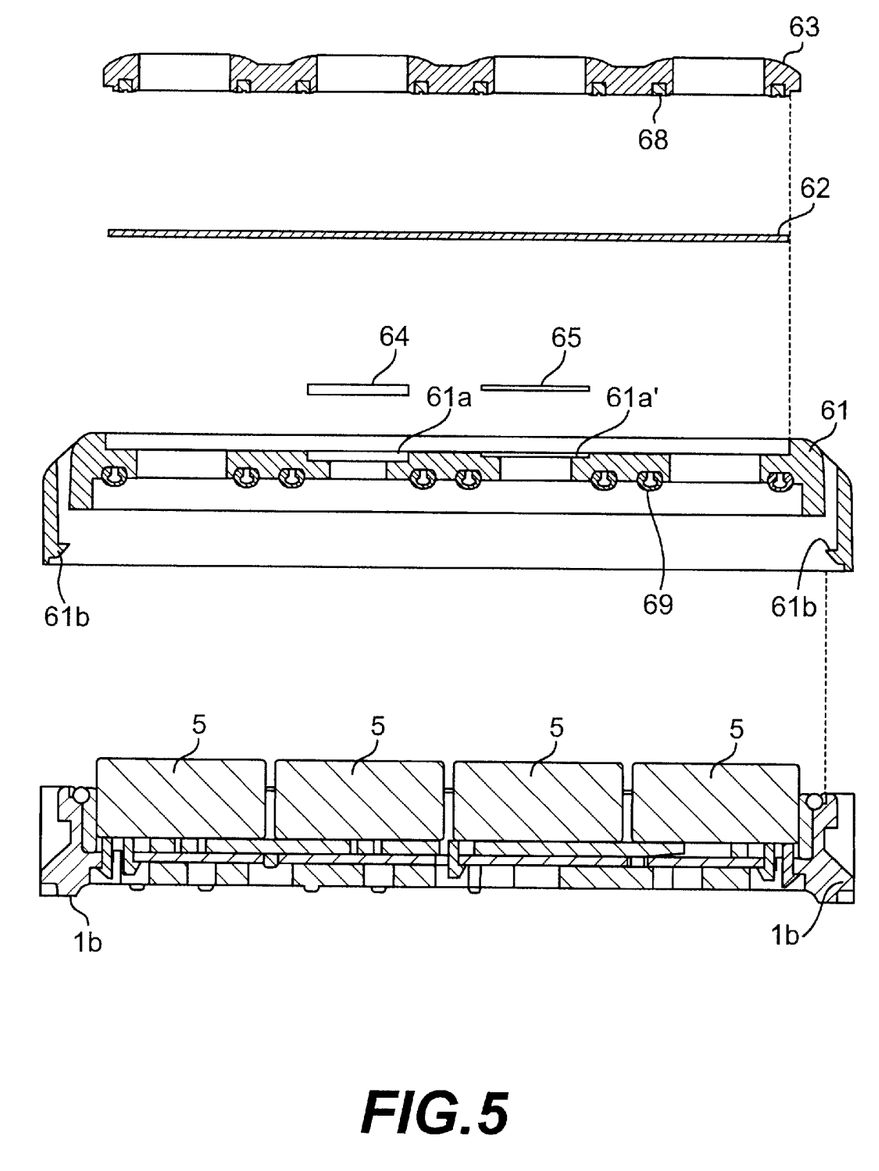
FIG. 5 is a cross-sectional view showing an embodiment of a framework constituting said gas-sensor holder.
Figure 6:
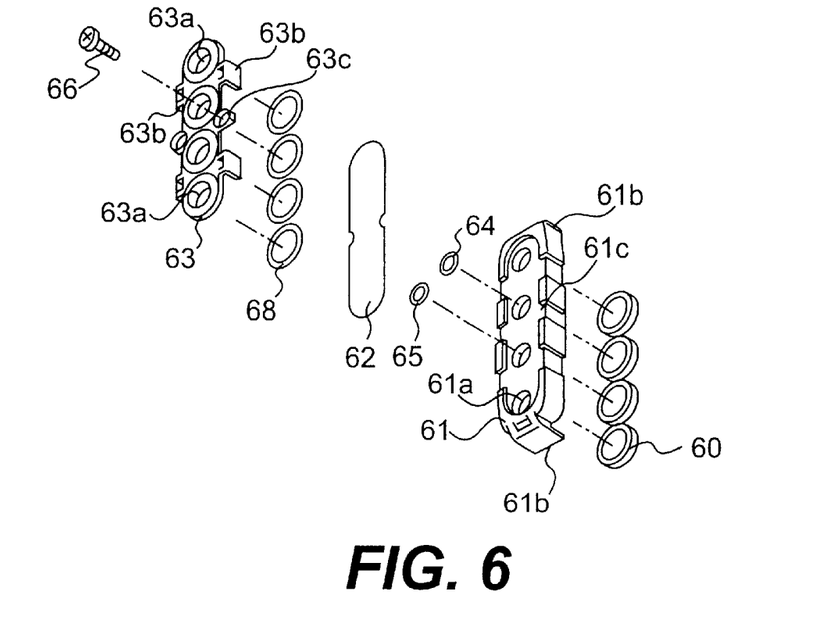
FIG. 6 is a perspective view showing an embodiment of the gas-sensor holder.

Recesses 12 are provided on one side of the casing proper 1 to accommodate multiple button-type gas sensors 5 to detect different kinds of gases, as shown in FIG. 4. A sensor-fastening frame 61 having windows 61a, 61a' to separate the gas intakes of the individual gas sensors is fitted to the casing proper 1 by the engagement of hooks 61b at both ends thereof with projections 1c on the casing proper 1.

A filter-fastening frame 63 holding a common dust-catching filter 62 to remove dust from the atmosphere admitted into the gas sensors 5 is placed on the surface of the sensor-fastening frame 61. The filter-fastening frame 63 has gas intakes 63a facing the individual gas sensors and is fastened to the sensor-fastening frame 61 by four hooks 63b provided on both sides thereof. As the presence of interfering gases may affect some sensors, filters 64 and 65 to remove such interfering gases are interposed between the sensor-fastening frame 61 and the dust-catching filter 62.

The stacked two fastening frames 61 and 63 are fastened to the casing 1 by driving bolts 66 into through holes 61c and 63c provided therein. Reference numerals 68 and 69 designate annular packing.

Figure 7:
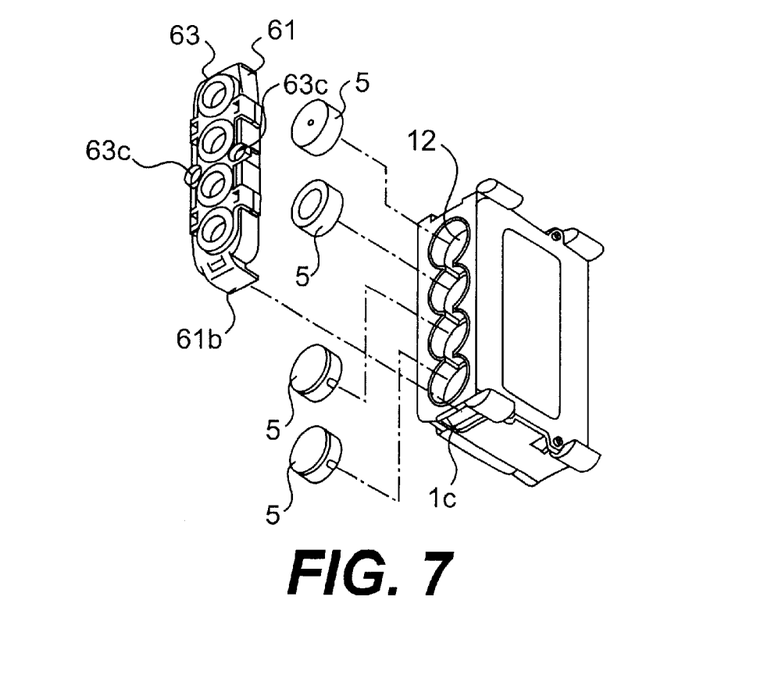
FIG. 7 shows a condition in which the gas sensors are changed.

The design allows easy change of gas sensors 5 when their sensitivity has dropped with prolonged use by unfastening the bolts 66 and removing the fastening frames 61 and 63 from the casing proper 1. When the filters 62, 64 and 65 malfunction, they can be easily changed by removing the filter-fastening frame 63. Removing the filter-fastening frame 63 can easily change the dust-catching filter 62 and interfering-gas removing filters 64 and 65.

Referring again to FIG. 1, charging contacts 13 to be connected to charging terminals 38 of the power supply unit 3 and a window for infrared communication 14 are provided on the other side of the casing proper 1.

Figure 8A:
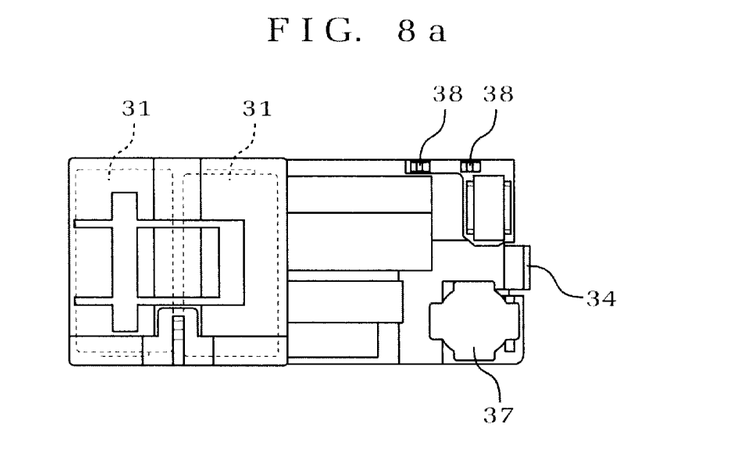
FIGS. 8a to 8c show an embodiment of the power supply unit for the same gas detector.
Figure 8B:
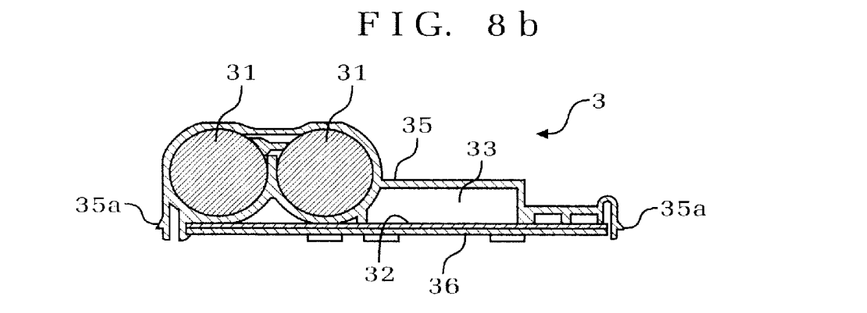
Figure 8C:
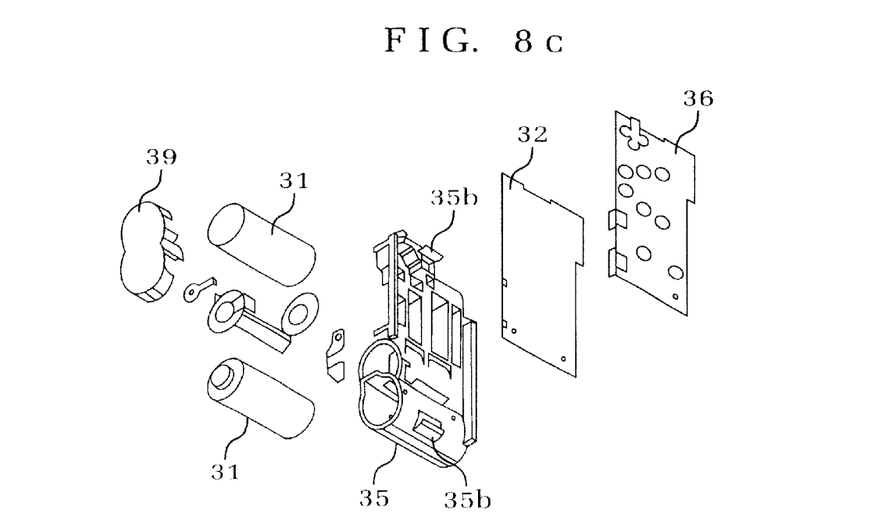

FIGS. 8a to 8c show an embodiment of the power supply unit 3 having secondary cells 31 mounted on a board 32. The terminals of the secondary cells 31 are connected to a connector 34 by way of a current-limiting resistor 33 that is connected in series. The parts involved in power supply, such as the cells, current-limiting resistor 33 and a conducting circuit pattern are covered with a top cover 35 having hooks 35a to engage with recesses 1d in the casing proper 1 and a bottom plate 36. The top cover 35 has inwardly protruding projections 35b that fasten the bottom plate 36. Reference numerals 37, 38 and 39 denote a back-up cell, charging terminals and a battery cover.

Figure 9:
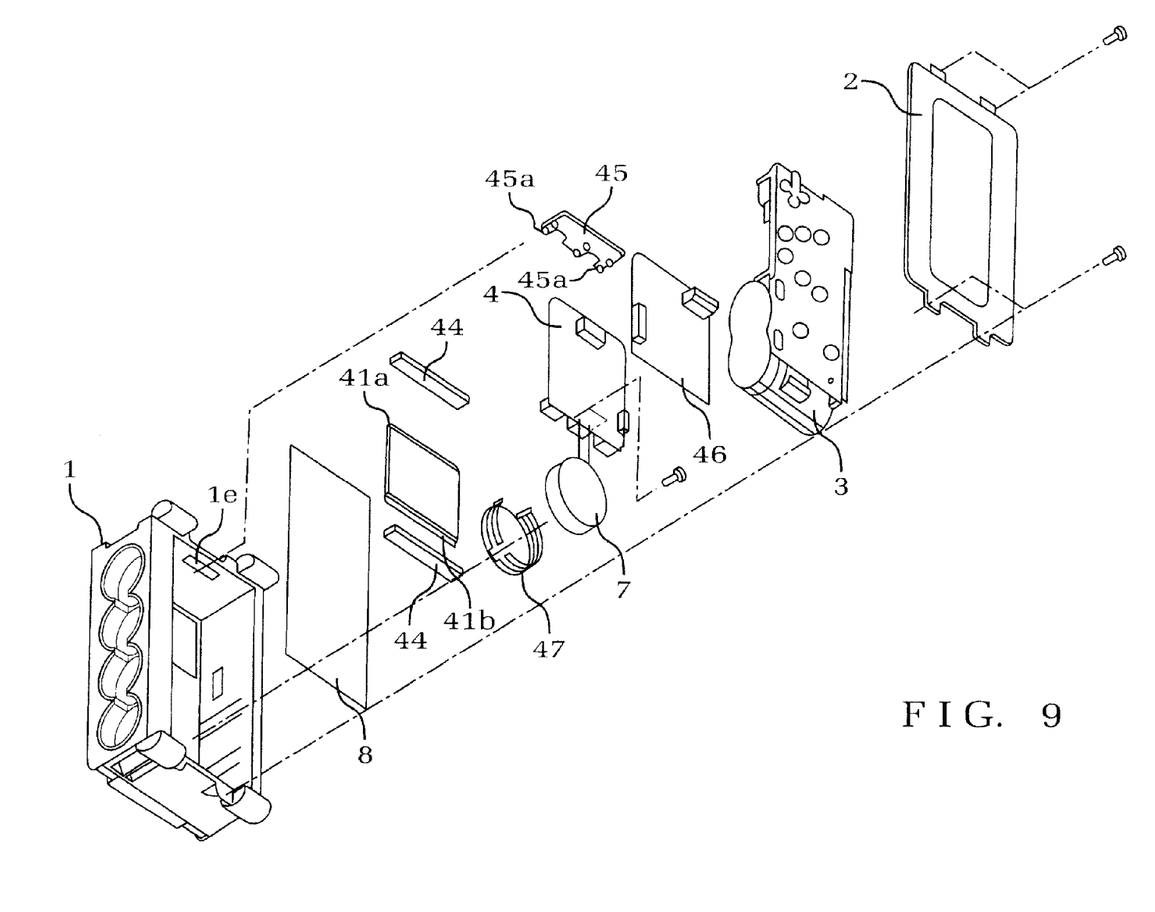
FIG. 9 shows the process of assembling the parts of the same gas detector.
Figure 10:
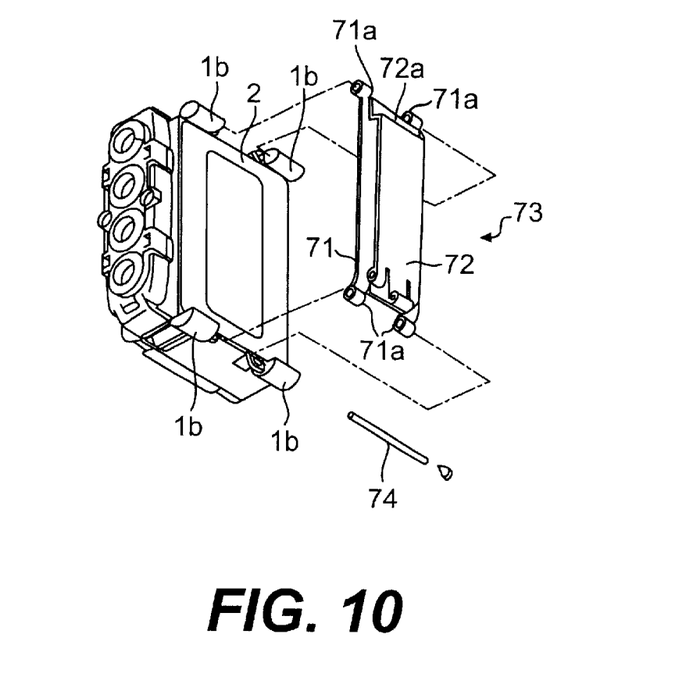
FIG. 10 shows another embodiment of the gas-sensor holder for the same small gas detector.

Now the process of assembling the gas detector just described will be described by reference to FIG. 9.

The casing proper 1 has a recess 1e, on the side (the upper end in the drawing) on which the liquid-crystal display panel is mounted, that is brought into engagement with a projection, not shown, on the back of a fastener 45 described later. First, the liquid-crystal display panel 41 having electrodes 41a and 41b on both sides (the top and bottom ends in the drawing) of the back thereof is mounted. The liquid-crystal display panel 41 is preferably backlit by light-emitting diodes or other similar means provided on both sides thereof through a scattering filter.

Connecting members 44 made of anisotropic conductive rubber (which is a material prepared by mixing a particulate conductive material with rubber or other similar insulant, having an extremely high electric resistance when no pressure is applied but exhibiting a localized electrical conductivity in a region subjected to a localized pressure in which the distance between the particulate conductive material becomes shorter to lower insulation resistance). The signal-processing unit 4 including a liquid-crystal activating circuit having electrodes is placed opposite the connecting members 44. The signal-processing unit 4 in this state is vertically pressed to insert the fastener 45 whose width is almost equal to that of the signal-processing unit 4 in the recess 1e in the casing proper 1. Then, multiple projections 45a formed on the surface of the connecting members 44 fasten the signal-processing unit 4 to the casing proper 1, with the connecting members 44 resiliently pressed thereby.

After mounting a connector board 46 carrying connectors to connect the signal-processing unit 4 with the power supply unit 3 and the outside and the power supply unit 3, the cover 2 is fastened to the casing proper with bolts or other similar means after placing a packing 3 along the edge of the opening thereof.

No force to tilt the connecting members 44 act because the fastener 45 is placed in position while the connecting members 44 are resiliently pressed in a direction perpendicular to the liquid-crystal display panel 41 and the signal-processing unit 4, with the connecting member 44 of anisotropic conductive rubber placed therebetween. This arrangement eliminates the need for bolts or other fastening means and permits establishing electrical connection therebetween without causing electrical leakage across the electrodes that are disposed close to the inner wall of the casing proper 1 and at small intervals with each other. Reference numeral 47 in the drawing designates a frame for fastening the sound-generating element 7.

This design permits fastening the power supply unit 3 to the casing proper 1 without requiring bolts. Also, removing the cover 2 and disengaging the hooks 35a from the recesses 1d can easily change the power supply unit.

When gases in the environment flow into the gas sensors 5 in the small gas detector fastened about the wrist, the gas sensors 5 react thereto and generate signals corresponding to the concentrations of the individual gases.

The circuit in the signal-processing unit 4 receives the signals form the gas sensors 5, stores the concentrations of the gases at each time point in the memory, and indicates the concentration of the gas selected by the external control switches on the liquid-crystal display panel 41. It is also possible to show the time by manipulating the external control switch as required.

When the concentration of any gas detected by the gas sensors 5 exceeds the preset standard level, the light-emitting elements 43 flash, the sound generating element 7 sounds an alarm, and the liquid-crystal display panel 41 automatically indicates the concentration of the gas in question.

The embodiment just described has a band to fasten about the wrist that is attached to the band receptacles 1b. A fastener 73 comprising a resilient leaf 72 extending between the band receptacles 1b, with one end 72a thereof cantilevered to a base plate 71, and fastened to the band receptacles 1b by bolts 74 driven into fastening holes 71a at both ends thereof permits the gas detector to be easily attached to the clothing.

If the sound-generating element 4 has a capacity to produce low-frequency vibrations of the order of a few tens of cycles per second (hertz), the resilient leaf 72 vibrates at high amplitudes by resonating with the vibrations transmitted through the casing proper 1, whereby the alarm is amplified and transmitted with greater certainty.

Figure 11A:
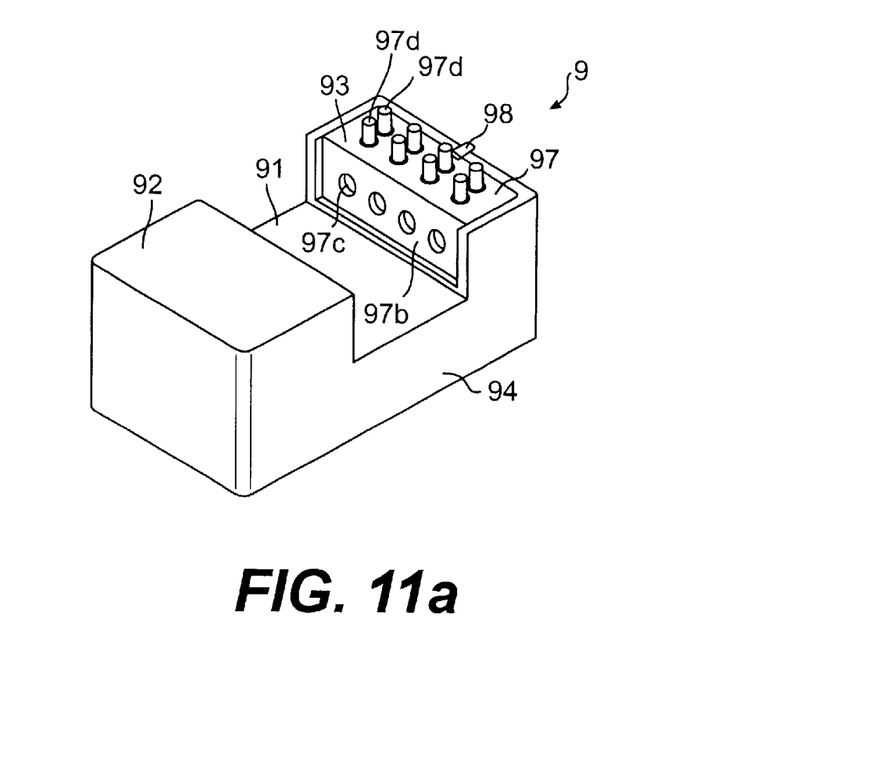
FIGS. 11a to 11c are a perspective view, a top view and a cross-sectional view showing the principal parts of a cradle suited for use with the gas detector described above.
Figure 11B:
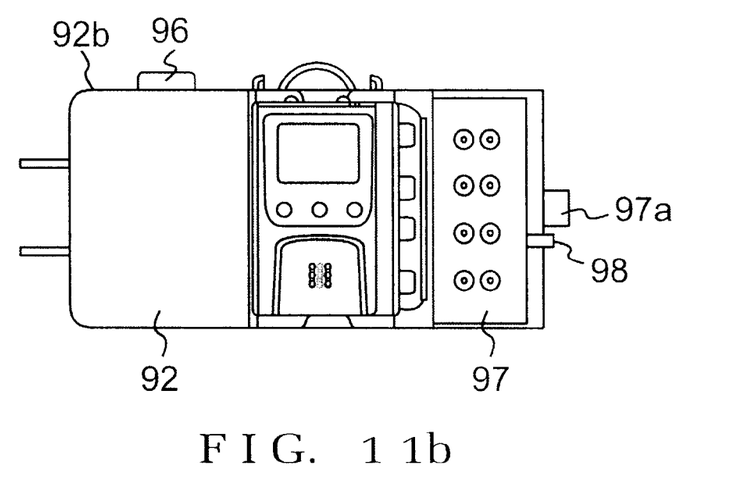

FIGS. 1a to 11c show an embodiment of the cradle 9 suited for use with the small gas detector just described. The cradle 9 comprises a base 94 on which are provided a center recess 91 whose width is somewhat larger than that of the gas detector, a segment 92 to accommodate the power supply circuit and other components on one side, and a calibration gas supply unit 93 on the other.

Figure 11C:
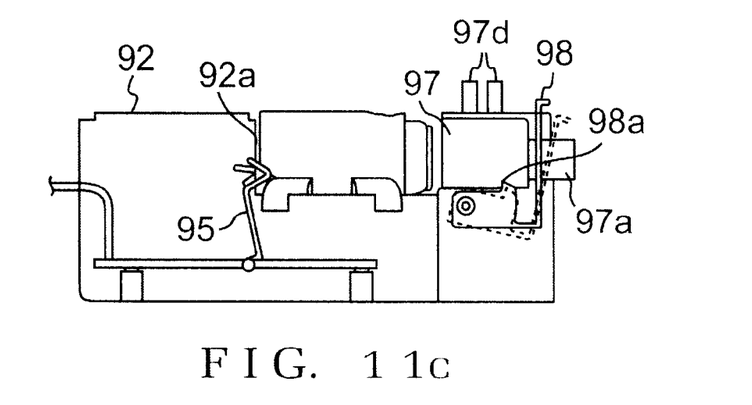

Two retractable electrodes 95 made of resilient conductive material are provided on one wall 92a of accommodating segment 92 closer to the recess, while a communication connector 96 for communication with the outside is provided on the other wall 92b.

The calibration gas supply unit 93 is normally pressed by a spring so as to retreat from the recess 91, with a slider 97 having a push rod 97a provided on the outer end thereof. The slider 97 has multiple windows 97 provided in the wall 97b facing the recess 91 in conformity with the arrangement of the gas sensors in the gas detector and gas supply ports 97d that separately supply reference gases to the individual windows 97c.

A hook 98a having a lever 98 that is normally pressed toward the slider and permits manipulation from outside is provided in an area facing the rear end of the slider 98.

When the cells 31 are consumed after a long period of use, the slider 97 can be fastened by the hook 98a while pressing one side of the small gas detector when the push rod is pressed, with the small gas detector mounted in the recess in the cradle.

In this state, the secondary cells 31 can be re-charged and internal data can be read by mans of the infrared communication means as the two electrodes 95 are in contact with the charging terminals 37 of the power supply unit 3 exposed through the windows 13. Also, calibration can be performed by supplying reference gases from the gas supply ports 97d to the gas sensors 5 through the windows 97c.

When the lever 98 is pressed down after the operation on the cradle is completed, the slider 97 retracts on being pushed by the force of the spring to release the small gas detector ready for removal.

When the secondary cells 31 have deteriorated through a long period of use, the power supply unit 3 can be replaced by disengaging the hooks 35a on the cover 35 from the casing proper 1. Even if any conductive substance comes into contact with the charging terminals 38 of the power unit, the current-limiting resistor 33 provided between the charging terminals 38 prevents the risk of fire even in the presence of combustible gases. Even if the power unit 3 is dropped by accident and the parts contained therein come in contact with any conductive substance, the cover 35 protecting the parts avoids short-circuiting and the risk of explosion in the presence of combustible gases.

Figure 12:
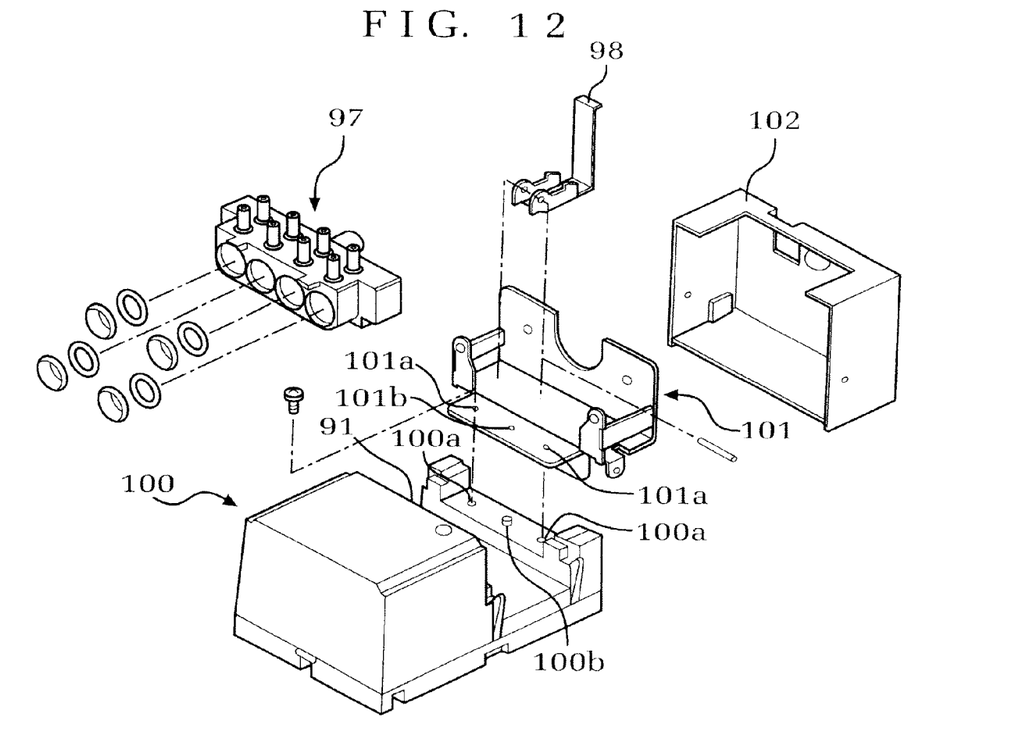
FIG. 12 shows another embodiment of the cradle.

While the cradle just described has charging, communication and gas calibration functions, another cradle 100 has only charging and communication functions as shown in FIG. 12. The gas calibration unit may be added as an option.

An optional gas calibration unit comprises a slider 97 movably mounted on a base 101 having bolt holes 101a and a recess 101b corresponding to bolt holes 100a and a positioning projection 100b on a cradle proper 100, the slider 97 being adapted to be halted by a lever 98. A cover 102 is bolted to the base 101.

This embodiment permits adding a gas calibration function to the cradle proper 100 having only charging and communication functions by bolting the optional unit just described.

What is claimed is:

1. A portable gas detector comprising a casing attachable to the human body, wherein said casing comprises a container proper and a cover made of high polymer, with part of a surface of said container proper being covered with a sheet of electrically conductive material, said casing having openings on one side to accommodate multiple gas sensors capable of detecting various kinds of gases, wherein the gas sensors are attached by a common sensor-fastening frame so as to be detachable, and said casing having charging and communication terminals on another side.

2. A portable gas detector according to claim 1, wherein said charging terminals, secondary cells and a current-limiting resistor are mounted on a circuit board, with said secondary cells and said current-limiting resistor being contained in a power supply unit covered with top and bottom covers of insulating material having means for fastening to said casing.

3. A portable gas detector according to claim 2, in which said charging terminals are exposed through windows provided in said casing.

4. A portable gas detector according to claim 1, wherein a common dust-catching filter is fastened to gas intakes in said openings by means of a fastening frame.

5. A portable gas detector comprising:

a casing attachable to the human body, said casing having openings on one side to accommodate multiple gas sensors capable of detecting various kinds of gases, wherein the gas sensors are attached by a common sensor-fastening frame so as to be detachable, and said casing having charging and communication terminals on another side;

band receptacles on two other sides of said casing; and a fastener comprising a resilient leaf having one end thereof cantilevered to a base plate, wherein said fastener is fastened to said band receptacles for fastening bands so as to be detachable.

* * * * *